United States Patent [19]

Klar et al.

[11] 4,002,161
[45] Jan. 11, 1977

[54] AUTOMATIC MEANS FOR TYMPANOMETRIC TESTING

[75] Inventors: Irwin Klar, New City; Erwin H. Rock, Dobbs Ferry, both of N.Y.; Arthur W. Rochussen, Nashua, N.H.

[73] Assignee: American Electromedics Corporation, Dobbs Ferry, N.Y.

[22] Filed: Dec. 2, 1975

[21] Appl. No.: 637,008

[52] U.S. Cl. .................................. 128/2 Z; 73/553; 179/1 N
[51] Int. Cl.² .......................................... A61B 5/12
[58] Field of Search ............. 128/2 Z, 2 R; 73/553; 179/1 N

[56] References Cited

UNITED STATES PATENTS

| | | |
|---|---|---|
| 2,415,310 | 2/1947 | Summerville et al. ............. 128/2 Z |
| 3,395,697 | 8/1968 | Mendelson ........................ 128/2 Z |
| 3,757,769 | 9/1973 | Arguimbau et al. ............... 128/2 Z |
| 3,882,848 | 5/1975 | Klar .................................. 128/2 Z |
| 3,949,735 | 4/1976 | Klar et al. ......................... 128/2 Z |

Primary Examiner—Kyle L. Howell
Attorney, Agent, or Firm—Holland, Armstrong, Wilkie & Previto

[57] ABSTRACT

An instrument is described which automatically performs a tympanometric hearing test and which gives the test results in graphic form. The test instrument includes a probe which is placed in the subject's ear and which applies controlled air pressure and audio test signals to a sealed ear canal in a manner programmed by the instrument so that a plot of the ear compliance versus the ear pressure is produced on the chart. The plot is made using a coordinated chart drive and ear probe air pressure control and an audio signal generator and a compliance signal level recorder. The system automatically runs through the necessary coordinated chart advance, air pressure control, and compliance signal recordings on the chart to complete one tympanometric test after the start button is operated.

21 Claims, 10 Drawing Figures

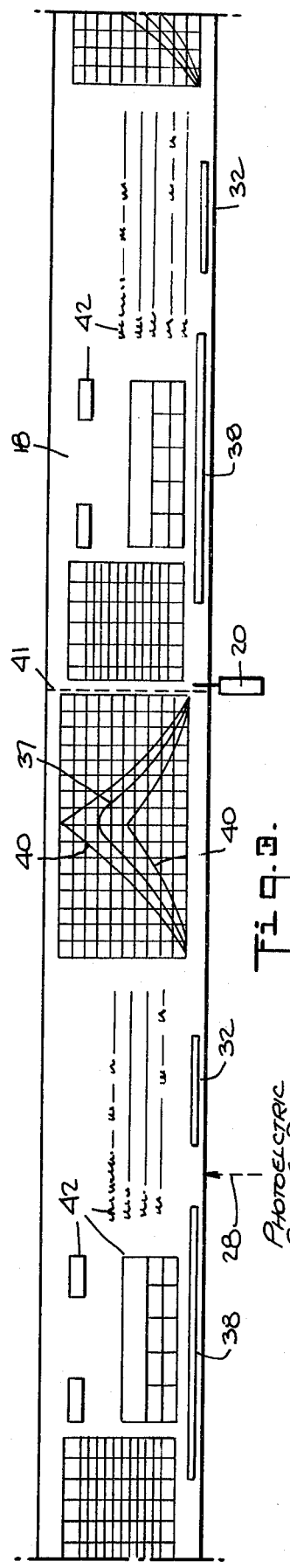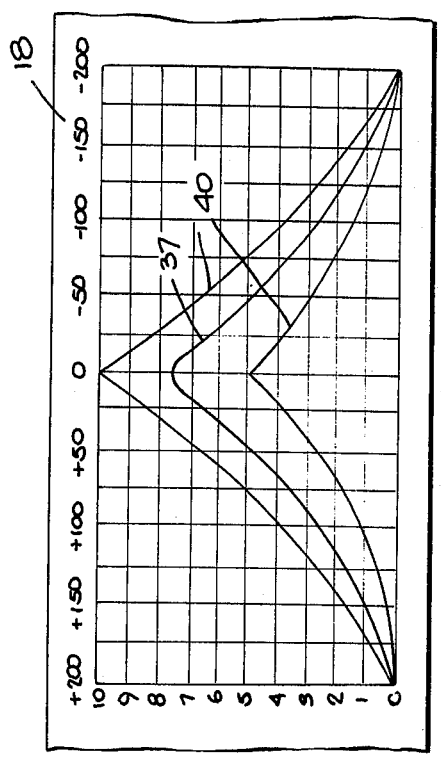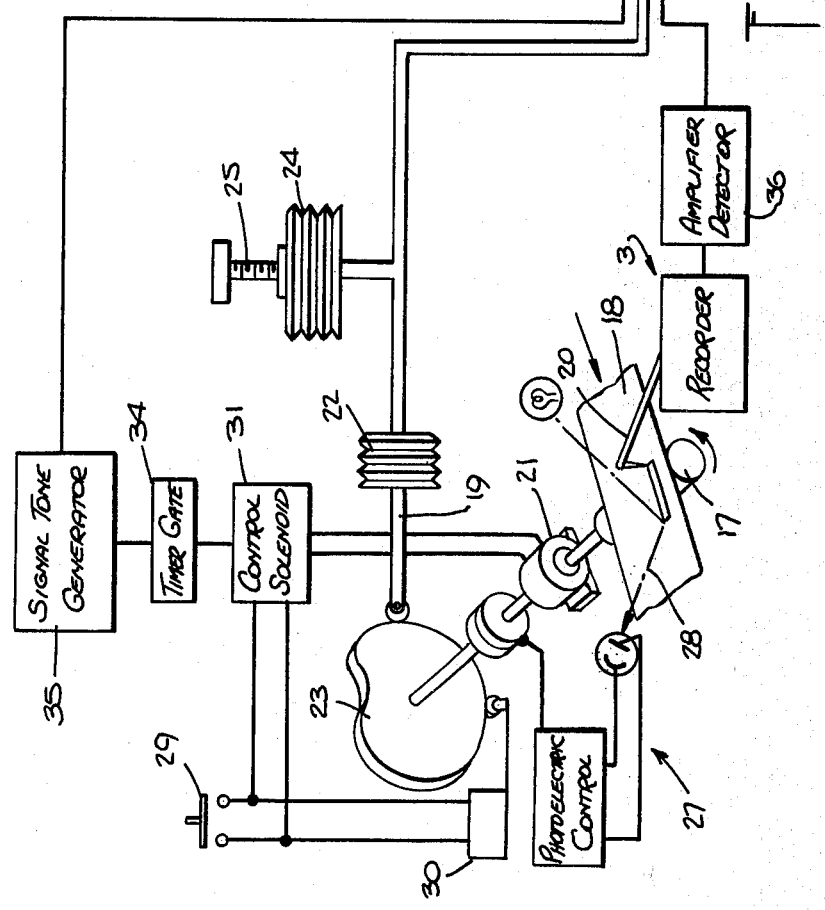

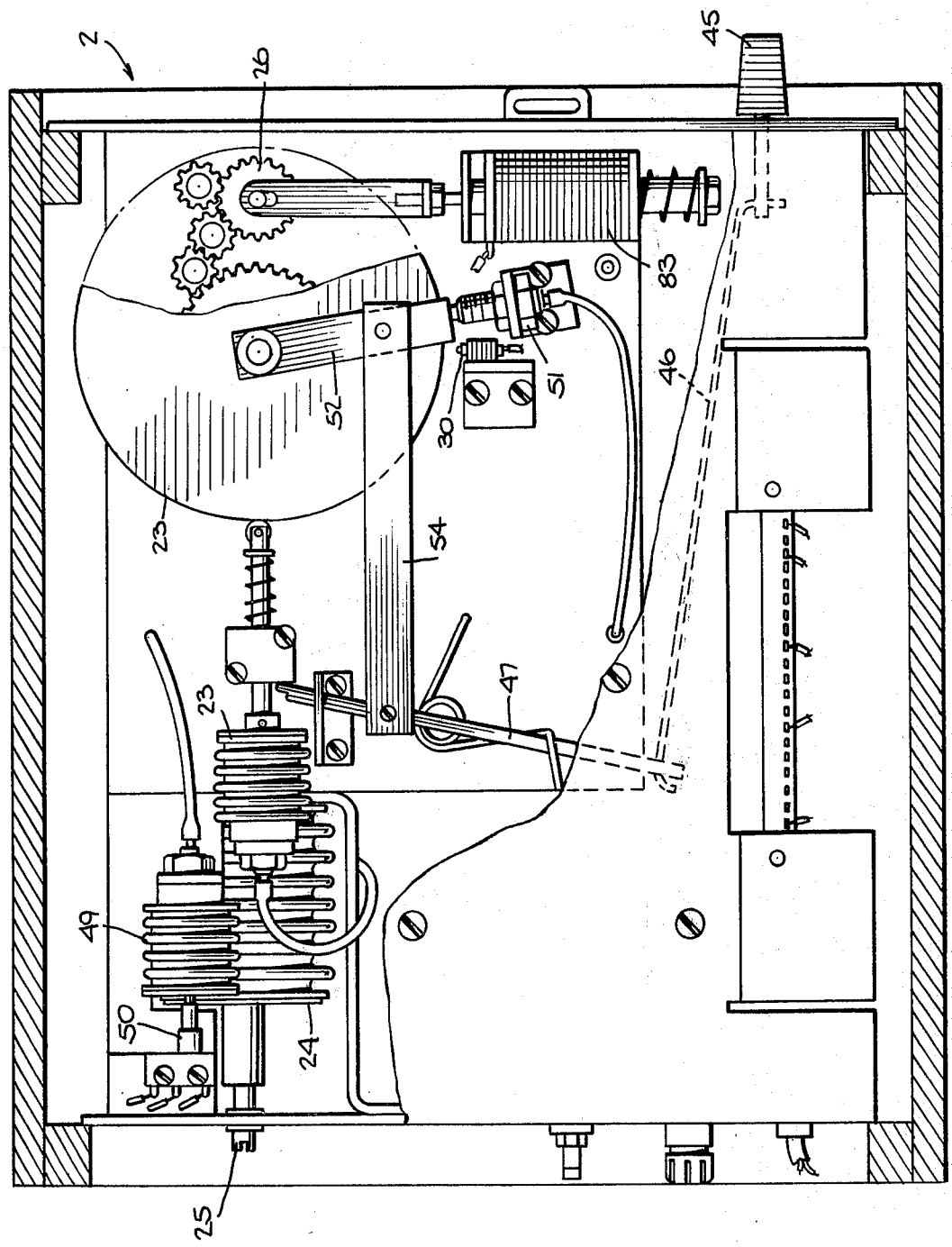

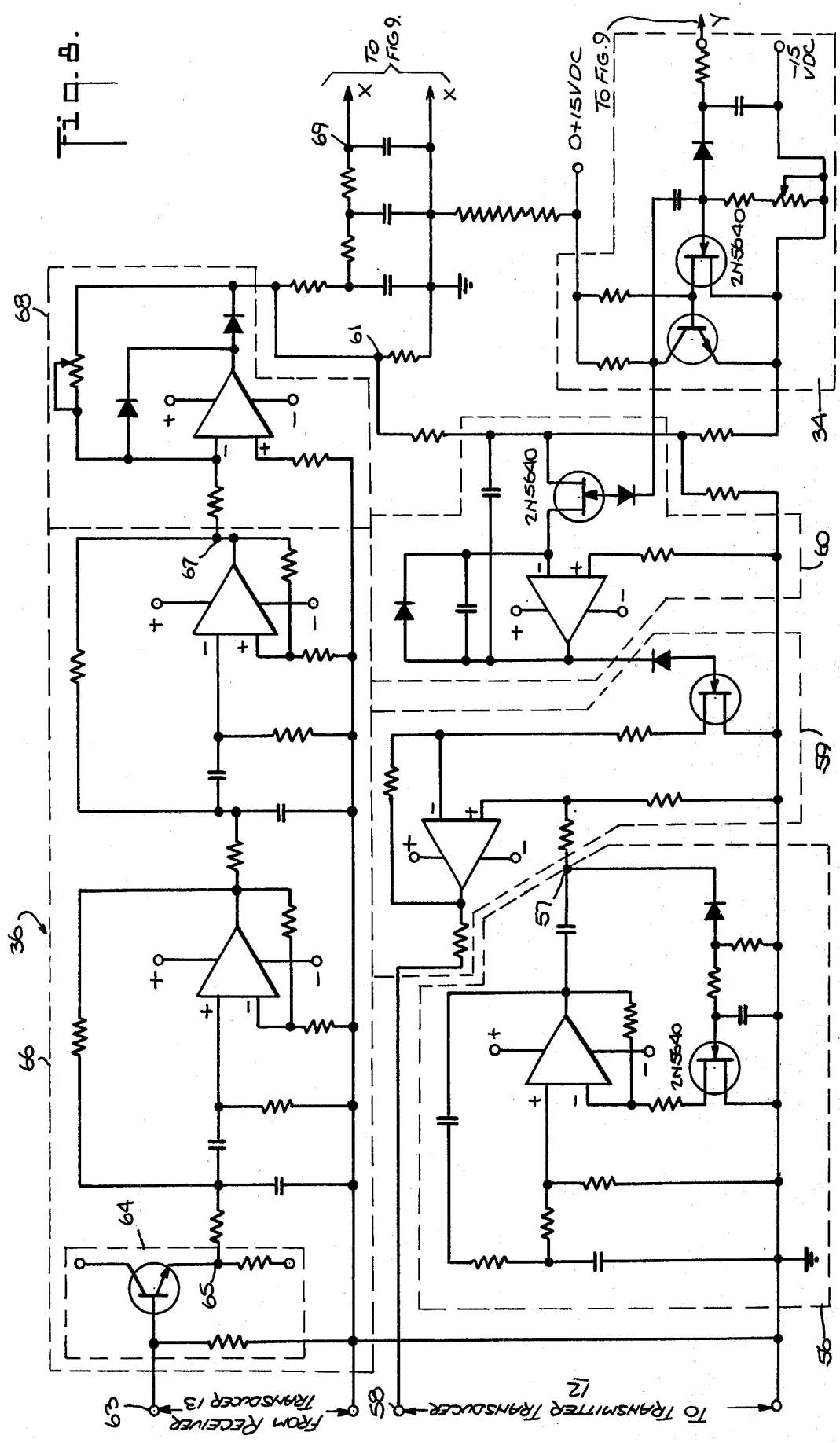

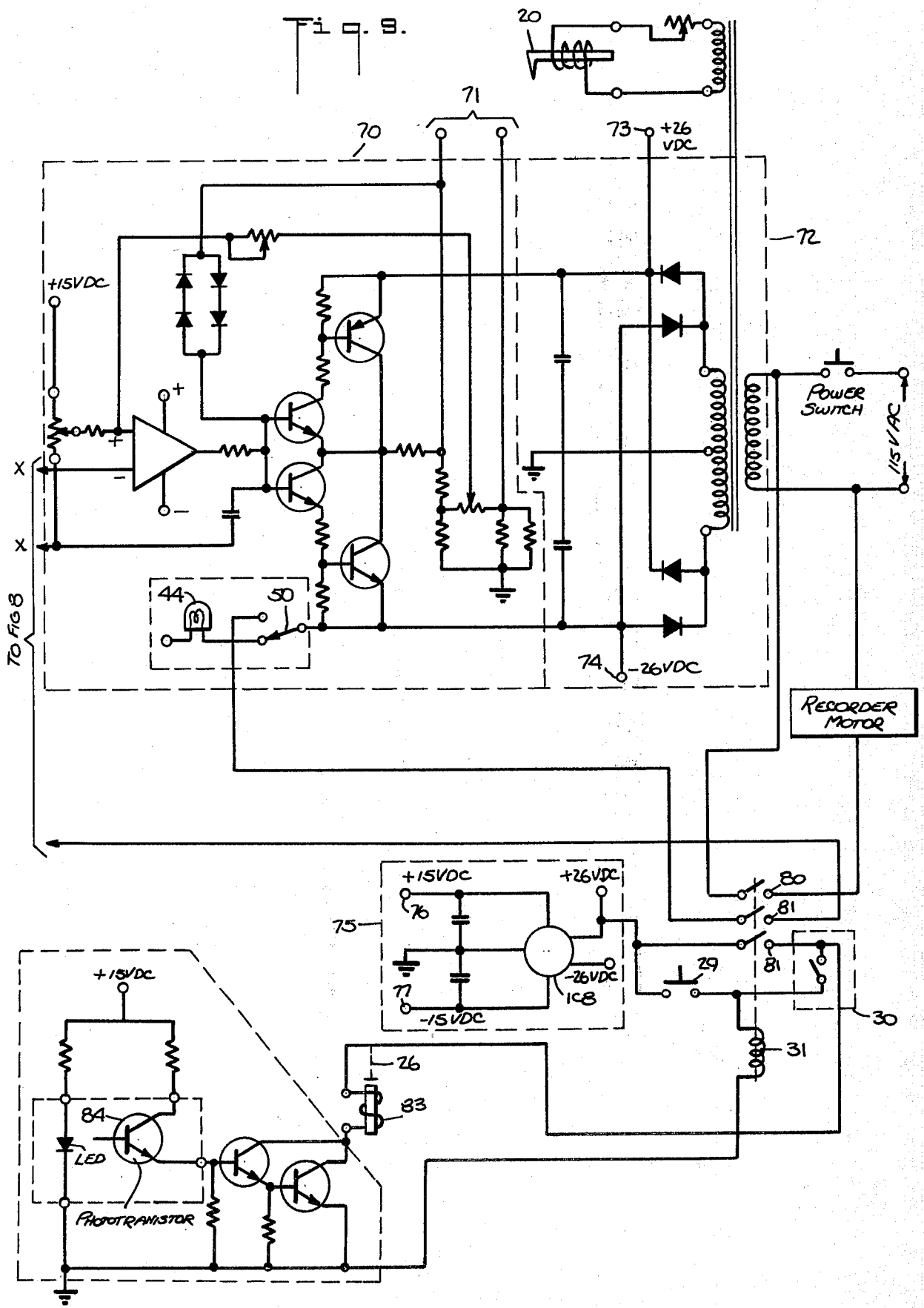

AUTOMATIC MEANS FOR TYMPANOMETRIC TESTING

BACKGROUND OF THE INVENTION

The present invention relates to an automatic instrument for testing bearing and more particularly to an instrument for performing a test known as tympanometry.

Tympanometry is an objective method for evaluation of the mobility of the tympanic membrane and the functional condition of the middle ear and is the measurement of eardrum compliance change as air pressure is altered in the external auditory canal. These measurements are recorded on a graph which represents the compliance-air pressure function and which is known as a tympanogram.

A point of significance is that the tympanic membrane is at maximum compliance when the air pressure in the middle ear is equal to the air pressure in the external ear canal. Tympanometry provides an indirect measure of existing middle ear pressure by identifying the air pressure in the external auditory canal at which the eardrum shows its maximum compliance. For example, patients who have intact tympanic membranes, with no middle ear pathology and adequate eustachian tube function, will show maximum compliance on the tympanogram at atmospheric pressure or within 50 mm of atmospheric pressure. Patients with intact eardrums and poorly functioning eustachian tubes, will show maximum compliance of other air pressure values.

To obtain a tympanogram, a probe is placed in the patient's ear which is initially clamped into a position of poor mobility by introducing positive pressure (+200 mm H$_2$O) into the external ear canal. Then the air presure in the external ear canal is systematically reduced while changes in the compliance are observed and recorded. As the air pressure is reduced, The eardrum becomes more compliant. When the air pressure in the external canal is exactly the same as the air pressure in the middle air cavity, the compliance reaches its optimum.

As the air pressure is further reduced beyond the point of maximum compliance, an unbalance of air pressure on either side of the tympanic membrane is created and the eardrum begins to show reduced compliance again.

The clinical uses of tympanometry are many. This technique demonstrates abnormalities in the mobility of the tympanic membrane due to stiffness, flaccidity, or the presence of fluid in the middle ear cavity. The technique of tympanometry can be used to monitor healing of tympanic membrane grafts, post-stapedectomy cases, or follow-up of otitis media.

The apparatus of this invention is an instrument which performs the above described evaluation in an automated sequence providing the results in the form of a recording or tympanogram. The instrument permits an efficient and rapid test program to be carried out for groups, such as groups of school children, by relatively inexperienced personnel and in a manner which provides an easily read and preservable record of the test procedure. This makes an important hearing test available in a practical way for almost universal use and for use with younger persons since the automatic test requires no response from the patient.

Accordingly, an object of the present invention, therefore, is to provide an improved automatic apparatus for tympanometry.

Another object of the invention is to provide a fully automated means for tympanometry providing test results not requiring a response from the patient.

Another object of the invention is to provide an improved instrument for tympanometry permitting relatively rapid and reliable testing.

Another object of the invention is to provide an automatic tympanometric test means providing a recorded read-out.

Another object of the invention is to provide an apparatus for tympanometry which may be utilized by relatively inexperienced personnel for testing large numbers of patients.

Other and further objects of the invention will be obvious upon an understanding of the illustrative embodiment about to be described or will be indicated in the appended claims, and various advantages not referred to herein will occur to one skilled in the art upon employment of the invention in practice.

Brief Description of the Drawings

A preferred embodiment of the invention has been chosen for purposes of illustration and description and is shown in the accompanying drawings, forming a part of the specification, wherein:

FIGS. 3 and 3A are front elevational views of a preferred embodiment of the recording chart.

FIG. 4 is a diagrammatic illustration of the elements of the tympanometry test system.

FIG. 7 is a horizontal sectional view taken along line 7—7 on FIG. 1.

FIGS. 8 and 9 are schematic diagrams illustrating the audio signal generating circuit and the instrument control circuit.

Description of the Preferred Embodiment

Figure 1:
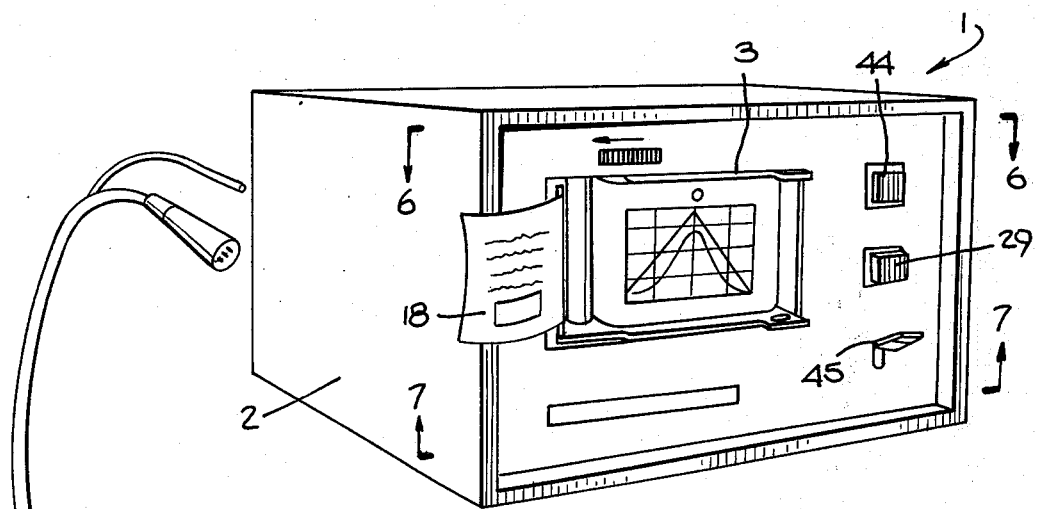
FIG. 1 is a perspective view illustrating a preferred embodiment of the instrument in accordance with the invention.
Figure 2:
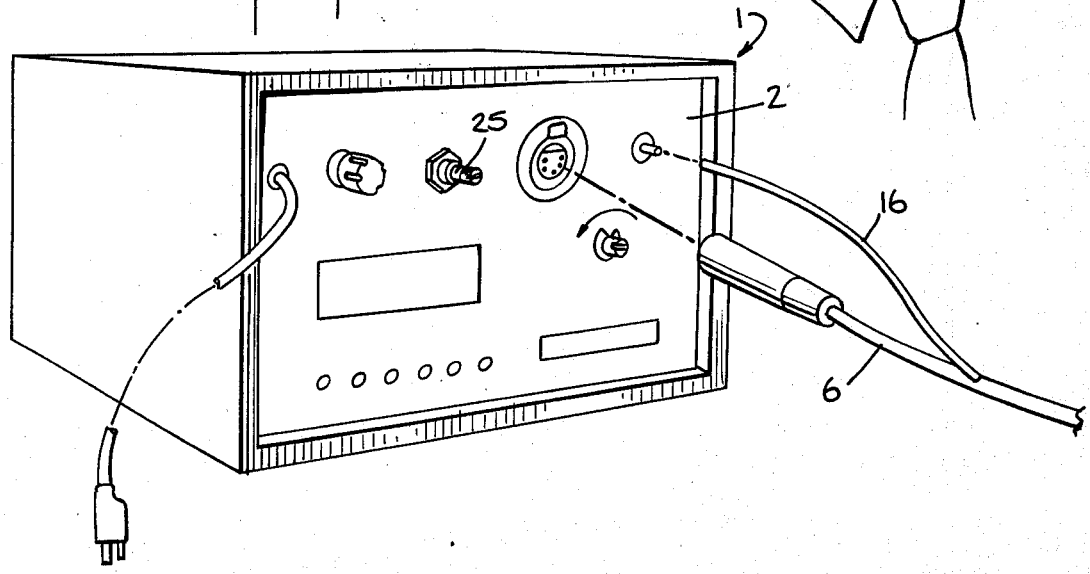
FIG. 2 is a perspective view illustrating the instrument connecting panel.

FIG. 1 illustrates the principal portions of the system 1 as used for tympanometry. A cabinet 2 contains the strip chart recorder 3 on which the recorded records are made. The cabinet 2 also contains an air pressure control means synchronized with the strip chart recorder 3 and an audio system which will be described below. The air system and the audio system in the cabinet 2 are coupled to a probe 4 mounted on a suitable headband 5 by a cable 6. The general function of these elements will now be briefly described with particular reference to the diagrammatic showing of these elements in FIG. 4.

In tympanometry, the probe 4 is inserted into the patient's outer ear canal 14 as diagrammatically illustrated at the right side of FIG. 4. The probe 4 includes a resilient sealing tip or cuff 7 to insure an airtight seal and the probe 4 supports three hollow coupling tubes 8, 9 and 10. These tubes extend to a transducer housing 11 placed at a convenient position adjacent the probe 4 as on the head band 5. The housing 11 includes a transmitting transducer 12 to convert the audio probe tone from an electrical signal to an audio signal and a transducer receiver 13 for receiving audio signal tones from the sealed ear canal 14 and for converting them to an electrical signal. A tubular coupling 15 connects the probe tube 9 through an air tube 16 to the air pressure system.

The automatic tympanometry apparatus of this invention provides the air inputs and the electrical signal measurements for the automatic cycle described generally above. As already indicated, the test varies the air pressure within the sealed ear canal 14 while measuring the portion of the probe tone received at the receiver transducer 13 during the pressure changes. The left side of FIG. 4 diagrammatically illustrates the apparatus of the invention incorporated in the cabinet 2.

There are three principal sub-systems within the cabinet 2. The first of these comprises the recorder 3 which includes drive roller means 17 for drawing a chart 18 from a suitable scroll supply. The recorder 3 records the test signals on the moving chart 18. A preferred chart 18, for example, may be a thermally sensitive recorder paper used with a galvanometric pen motor driving a heated stylus 20. The chart 18 is driven by an electric drive motor 21.

The second principal sub-system comprises the air pressure control system coupled to the probe 4 air supply tube 16 for changing the air pressure within the sealed ear canal 24 through the desired test pressures during a test cycle. The preferred air pressure system comprises a piston 19 operating a bellows 22 from a rotating control cam 23. A buffer bellows 24 of relatively large air capacity is included in the system to increase the system size and thereby minimize any errors resulting from changes in the sealed ear canal size. An adjusting screw 25 permits the air system to be adjusted to compensate for the altitude, i.e. ambient air pressure of the test site. The size of the bellows system and movement of bellows 22 by the cam 23 are set to give a predetermined air pressure variation through a test cycle which occurs during one rotation of the air pressure control cam 23.

In order to permit independent movement of the chart 18 and the control cam 23 during a test cycle, as will be more fully described below, a clutch 26 controlled by a photoelectric system 27 connects the cam 23 to the chart drive motor.

The other principal portion of the tympanometry apparatus comprises the electrical control and audio test tone generating circuit and the tone compliance receiving and recorder driving circuits. This system includes a signal generator 35 operating at the desired frequency, such as 220 Hertz, which is coupled to the transmitter transducer 12 to feed the probe tone into the ear probe 4. It also includes an amplifier and detector 36 coupled to the receiver transducer 13 for operating the recorder 3 to record the compliance values.

Movement of the chart 18 independently of the rotation of the pressure control cam 23 is obtained by the photoelectric system 27 employing darkened control indicia on the chart 18 which interrupts the system 27 beam 28 at certain chart positions during the test cycle. The photoelectric control 33 opens and closes the cam clutch 26.

A test cycle is initiated by a start switch 29 and is terminated by a latching switch 30 connected in parallel and operated by the control cam 23.

A test cycle will now be described with further reference to FIG. 4. After the probe 4 has been placed in the test subject's ear and a seal obtained, the test cycle is initiated by activation of the start switch 29 on the tympanometry cabinet 2. The switch 29 energizes the chart drive motor 21 through the control solenoid 31 initiating chart 18 motion. As seen in FIG. 3, the photoelectric system beam 28 at the start is adjacent a clear portion of the chart 18 so that the cam control clutch 26 remains closed for a short interval during a corresponding initial rotation of the cam 23. This rotation is sufficient to close the latching switch 30 permitting the motor 21 to continue running as the start switch 29 is then opened.

Almost immediately thereafter, the chart 18 advances a control indicia 32 into the beam 28 causing it to open the clutch 26 through the control circuit 33. The chart 18 continues to advance permitting the drive motor 21 to accelerate to a constant drive speed to insure constant chart speed during the test. When the chart 18 moves the indicia 32 beyond the beam 28, the photocell control 33 is activated to close the cam drive clutch 26 causing further rotation of the cam 23 so that it moves the air bellows 22 through the desired pressure changes in accordance with the shaping of the cam 23 surface. The cam 23 is shaped so that the piston 19 operates the bellows 22 to increase the system pressure to +200 mm of water at the instant that the chart reaches the +200 indication as seen in FIG. 3A. At this instant, the gate and timer system 34 is activated by the air pressure switch 50 placing the tone generator 35 in the test mode. In this mode, the AGC is disabled and a constant level of 220 Hertz signal is fed to the probe 4.

At this time, the chart 18 is moving and the air pressure in the sealed ear has been raised to the desired 200 mm of water. The tympanometry test will now be carried out as the chart 18 advances from the +200 reading to the −200 reading and the cam 23 adjusts the sealed ear pressure from +200 mm to −200 mm. The probe tone which is entering the sealed ear canal 14 through the tube 8 is being partially transmitted into the inner ear and partially returned through the transducer receiver 13 and the related amplifier detector 36 to the recorder 3.

FIG. 3A illustrates at 37 a typical response for a relatively normal ear during this period where a maximum transmission into the inner ear, i.e. minimum probe tone return, for a healthy membrane occurs near zero ear pressure and where a typical compliance change leading up to and leading away from the zero pressure position is recorded on the chart. Guide lines 40 preprinted on the chart 18 show an expected range for normal responses. After the chart 18 moves past the −200 mm position, it continues to advance and the air pressure control cam continues to rotate to return the system air pressure to zero by piston 19. When the zero air pressure point is reached for the cam 23 it is still desirable to advance the chart 18 to move it clear of the recording stylus 20 and to permit a completed chart to be conveniently torn off at tear lne 41 from the remaining strip in the cabinet 2. This result is obtained by the use of a second photocell controlling indicia 38 provided on the chart 18 which causes the photocell control 33 to open the cam drive clutch 26 thereby stopping the cam 23 while the paper drive roller 17 continues to move the chart 18 out of the cabinet 2 and clear of the recording area. When the chart 18 moves the indicia 38 beyond the beam 28, the clutch 26 is reclosed for a brief interval to turn the cam 23 just far enough to cause it to open the latching switch 30 thereby shutting off the drive motor 21 and leaving the apparatus ready for another tympanometry test. The chart 18 preferably includes additional printed data and blanks 42 for information pertinent to the test.

In order for the test to be satisfactory, it is necessary to have the probe 4 in sealed relationship with the ear canal 14 so that the air pressure will reach its desired +200 mm pressure at the commencement of the test and will follow the desired pressure reduction to −200 mm as the test progresses. An indicator lamp 44 is provided on the test cabinet which is extinguished when the pressure reaches the +200 mm.

Figure 5:
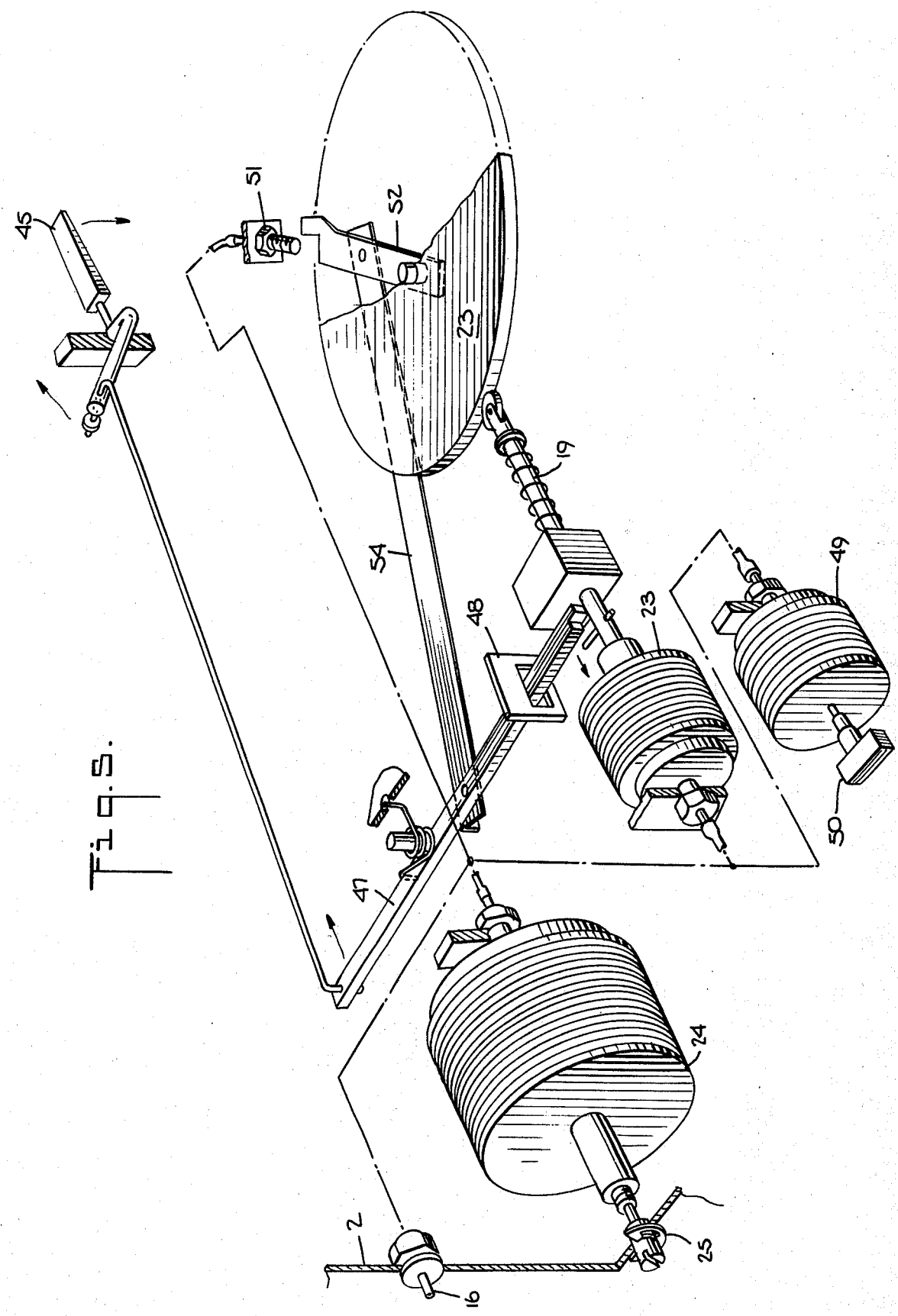
FIG. 5 is perspective view illustrating the interconnected elements of the air pressure control portion of the system.
Figure 6:
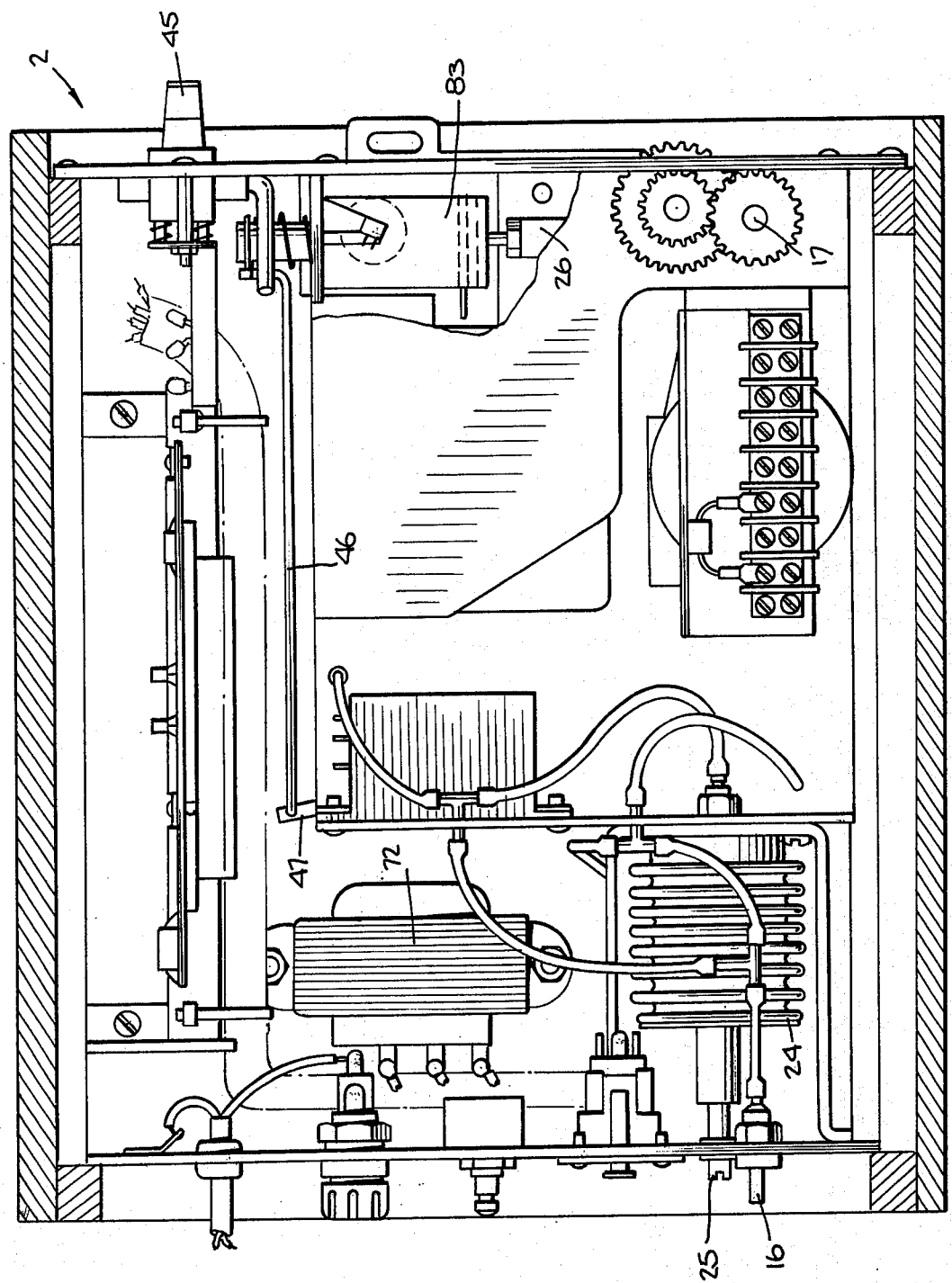
FIG. 6 is a horizontal sectional view of the preferred embodiment of the apparatus taken along line 6—6 on FIG. 1.

A pressure test means is incorporated with the indicator lamp 44 to test the ear seal prior to the commencement of the test cycle. This is illustrated in FIG. 5. It provides a manually operated lever 45 on the cabinet front which is coupled by a rod 46 and a pivotally mounted arm 47 to the pressure control piston 19. When the lever 45 is fully depressed as controlled by a mechanical stop 48, the bellows 23 is moved to its +200 mm position. This pressure increase to +200 mm is detected by a test bellows 49 which expands sufficiently to activate a micro switch 50 extinguishing the pressure test lamp 44. The same test bellows 49 operates during each test cycle as soon as the pressure in the sealed ear canal reaches to the +200 mm. When the test lamp 44 goes out as the chart 18 reaches the +200 mm position, the test knows that he has a properly sealed ear canal 14.

A pressure relief valve 51 which bleeds the air pressure system is incorporated in the air system. The cam 23 is shaped, to release and to open the valve 51 at the end of each operating cycle to insure a zero system pressure by bleeding the system. In order to permit the above described preliminary pressure test, the manual pressure test system includes a pivoted arm 52 positioned to engage and to close the relief valve 51 through the intermediation of a connecting link 54.

FIGS. 8 and 9 are diagrams of the preferred embodiment of the system circuit. The circuit comprises an interconnection of a number of known solid state circuits using conventional elements. The function and values for these elements will be apparent from the diagram so that detailed descriptions of the elements will be given only in certain cases to illustrate a preferred circuit.

In general, the function of the electrical portion of the instrument may be divided into two principal functions. One function is a chart driving and timing function which controls the start and stop of the paper drive together with a synchronized control of the test air pressure changes. A second function of the circuit comprises the generation and control of the audio probe test signal which is fed into the ear under test through the test probe and the detection and recording of the return compliance signal.

The signal generator 35 includes an audio oscillator 56 illustrated at the lower left hand corner of FIG. 8 operating at 220 Hertz. The output of the oscillator 56 is coupled at 57 to the transducer transmitter output 58 through an automatic gain control to establish a predetermined signal level at the tested ear such as 85 db. The AGC comprises a variable gain stage 59 and a gated intergrator 60 which are coupled at 61 to the amplified and rectified compliance signal to form a control feed back loop. A one shot timer gate 34 set for a test interval is coupled to the gated integrator to cut off its control action for the test interval or the coast mode. The one shot timer 34 is activated by the air pressure switch 50 so that the action of the timer 34 is started when the pressure reaches +200 mm H$_2$O. This arrangement stabilizes the tone generator level while allowing it to coast to get the varying compliance reading during the +200 mm to −200 mm test period. The signal received from the ear under test at the input terminal 63 is fed into a preamplifier 64 shown at the upper left side of FIG. 8 whose output is coupled at 65 to a tuned amplifier 66 for the 220 Hertz compliance signal. This amplifier operates effectively for noise rejection and its output is coupled at 67 to a precision rectifier 68 which is coupled through a filter 69 to a DC power or galvanometer 70 (FIG. 9) having a galvanometer coil input at 71.

A power rectifier 72 is illustrated at the right side of FIG. 11 which supplies the plus and minus 26 volt DC voltage at terminals 73 and 74 and powers a regulator 75 producing a controlled lower plus and minus 15 volt DC output at terminals 76 and 77 for use in other sections of the system as indicated.

The main control solenoid 31 is shown at the lower right hand corner of FIG. 9. The solenoid 31 operates under the control of the start switch 29 which couples it to the 26 volt DC source. As soon as the start switch 29 is closed, the three solenoid 31 contacts 80, 81 and 82 are closed. Contact 80 energizes the recorder drive motor 21. A second contact 81 is coupled to a 26 volt source through the air pressure switch 50. The switch 50, as described above, is closed by the auxiliary pressure measurement bellows 49 when the ear canal pressure has reached +200 mm. The switch 50 is thus closed when the main bellows has reached its maximum pressure position under the control of the air pressure cam 23. At this time, contact 81 causes the time gate 34 to be activated to initiate the test or coast mode interval during which time the sealed ear canal 14 is subjected to a constant 220 Hertz test probe tone. The third contat 82 on the control solenoid 31 is coupled through a clutch engaging solenoid 83 which controls the cam drive clutch 26 coupling the air pressure control cam 23 to the recorder motor 21. The clutch engaging solenoid 83 is energized to cause the pressure control cam 23 to turn except when the solenoid 83 is cut off by the photoelectric system 27. As described above, indicia on the chart 18 interrupt the chart scanning light beam to cause phototransistor 84 to open the solenoid 83 energizing circuit.

It will be seen that an improved instrument has been provided for automatically performing and recording a tympanometric test.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

Having thus described our invention, we claim:

1. An improved automatic means for tympanometric ear testing including an ear probe having means for transmitting and for receiving audio test signals and having an ear canal seal and an air transmission tube for controlling the sealed ear canal pressure in combination with a recorder including a recording chart with a drive means therefor, means for varying the air pressure in the sealed ear canal through said probe air transmission tube, means for synchronizing the variations of the air pressure with the movement of the driven recording chart, means for generating an audio frequency probe tone signal for said transmitting means, and means for coupling said probe signal receiving means to said recorder.

2. The means as claimed in claim 1 in which said chart drive comprises an electric drive motor, and said means for varying said pressure comprises an air pump coupled to said drive motor.

3. The means as claimed in claim 2 in which said synchronizing means comprises a cam actuated drive in the coupling between said motor and said pump.

4. The means as claimed in claim 2 which further comprises a clutch in said coupling between said motor and said air pump.

5. The means as claimed in claim 4 which further comprises photoelectric control means activated by indicia on the recording chart and coupled to said clutch for engaging and disengaging the clutch.

6. The means as claimed in claim 4 which further comprises a clutch in the coupling between said motor and said cam actuated drive.

7. The means as claimed in claim 2 in which said pump comprises a bellows.

8. The means as claimed in claim 7 which further comprises a second bellows coupled in said pressure varying means for enlarging the volume of the air pressure means to reduce the effect of minor volume variations in the sealed ear.

9. The means as claimed in claim 8 which further comprises means for adjusting the volume of said second bellows to adjust the air pressure means for ambient air pressure changes.

10. The means as claimed in claim 1 which further comprises a pressure indicator coupled to said air pressure varying means.

11. The means as claimed in claim 2 which further comprises a manually operated ear canal pressure adjusting means operated independently of said drive motor.

12. The means as claimed in claim 3 which further comprises means for bleeding said sealed ear canal coupled to said cam actuated drive.

13. The means as claimed in claim 1 in which said probe tone signal generator includes an automatic gain control.

14. The means as claimed in claim 13 which further comprises a timer for controlling the period of operation of said automatic gain control.

15. An improved automatic means for tympanometric ear testing including an ear probe having means for transmitting and for receiving audio test signals and having an ear canal seal and an air transmission tube for controlling the sealed ear canal pressure in combination with a recorder including a recording chart with a drive means therefor, a pump for varying the air pressure in the sealed ear canal through said probe air transmission tube, means for synchronizing the pump with the movement of the driven recording chart, said synchronizing means including a cam operated pump drive coupling the pump to a drive motor through a clutch, means for generating an audio frequency probe tone signal for said transmitting means, and means for coupling said probe signal receiving means to said recorder.

16. The means as claimed in claim 4 which further comprises photoelectric control means activated by indicia on the recording chart and coupled to said clutch for engaging and disengaging the clutch.

17. The means as claimed in claim 15 in which said pump comprises a bellows.

18. The means as claimed in claim 17 which further comprises a second bellows coupled in said pressure varying means for enlarging the volume of the air pressure means to reduce the effect of minor volume variations in the sealed ear.

19. The means as claimed in claim 18 which further comprises means for adjusting the volume of said second bellows to adjust the air pressure means for ambient air pressure changes.

20. The means as claimed in claim 15 in which said probe tone signal generator includes an automatic gain control.

21. The means as claimed in claim 20 which further comprises a timer for controlling the period of operation of said automatic gain control.

* * * * *